United States Patent [19]

Varnes et al.

[11] Patent Number: 4,973,247
[45] Date of Patent: Nov. 27, 1990

[54] DENTAL HANDPIECE ASSEMBLY

[76] Inventors: DeWayne L. Varnes, Rte. 1, Ridgeland, Wis. 54763; Leslie V. Martens, 6956 161st. La. NW., Anoka, Minn. 55303

[21] Appl. No.: 410,366

[22] Filed: Sep. 20, 1989

[51] Int. Cl.$^5$ .............................................. A61C 1/12
[52] U.S. Cl. ......................................... 433/85; 433/82
[58] Field of Search ............................. 433/85, 84, 82

[56] References Cited

U.S. PATENT DOCUMENTS

| | | | |
|---|---|---|---|
| 2,459,573 | 1/1949 | Morrow | 433/84 |
| 2,884,695 | 5/1957 | Ellis | 433/84 |
| 3,250,005 | 5/1966 | White | 433/85 |
| 3,394,458 | 7/1968 | Bustamente et al. | 433/84 |
| 3,505,737 | 4/1970 | Merolla | 433/82 |
| 3,640,277 | 2/1972 | Adelberg | 604/14.1 |
| 3,949,753 | 4/1976 | Dockhorn | 433/84 |
| 4,075,761 | 2/1978 | Behne et al. | 433/85 |
| 4,162,030 | 7/1979 | Capra et al. | 222/321 |
| 4,182,038 | 1/1980 | Fleer | 433/85 |
| 4,193,197 | 3/1980 | Kuris et al. | 433/82 |
| 4,220,446 | 9/1980 | Walker | 430/85 |
| 4,340,368 | 7/1982 | Lococo | 433/85 |
| 4,382,786 | 5/1983 | Lohn et al. | 433/83 |
| 4,470,812 | 9/1984 | Martens et al. | 433/85 |

FOREIGN PATENT DOCUMENTS 2614776 12/1977 Fed. Rep. of Germany .
561537 5/1975 Switzerland .

Primary Examiner—Paul J. Hirsch
Attorney, Agent, or Firm—Burd, Bartz & Gutenkauf

[57] ABSTRACT

A gas driven medical or dental handpiece assembly of the type having a turbine driven dental tool. A sterile coolant supply is usable with the handpiece to provide liquid fluid under pressure to irriagate the patient site and cool the dental tool. The coolant fluid is derived from a cartridge connected to the handpiece. The cartridge is replaced for each patient. The cartridge is divided by a flexible diaphragm into a propellant chamber and a liquid chamber. Initially the liquid chamber is full and the propellant chamber is empty with virtually a volume of zero. A propellant gas under pressure is introduced into the propellant chamber of the cartridge to displace the diaphragm and move the liquid through a fluid conduit to the tip of the handpiece. The propellant is derived from a portion of the compressed gas used to drive the turbine. Another portion of the compressed gas is diverted to a chip air conduit of the handpiece. The handpiece assembly eliminates the use of the conventional common water supply as irrigant or coolant fluid. Use of the removeable fluid cartridge allows sterilization of the entire handpiece eliminating much of the risk of cross contamination between patients.

21 Claims, 2 Drawing Sheets

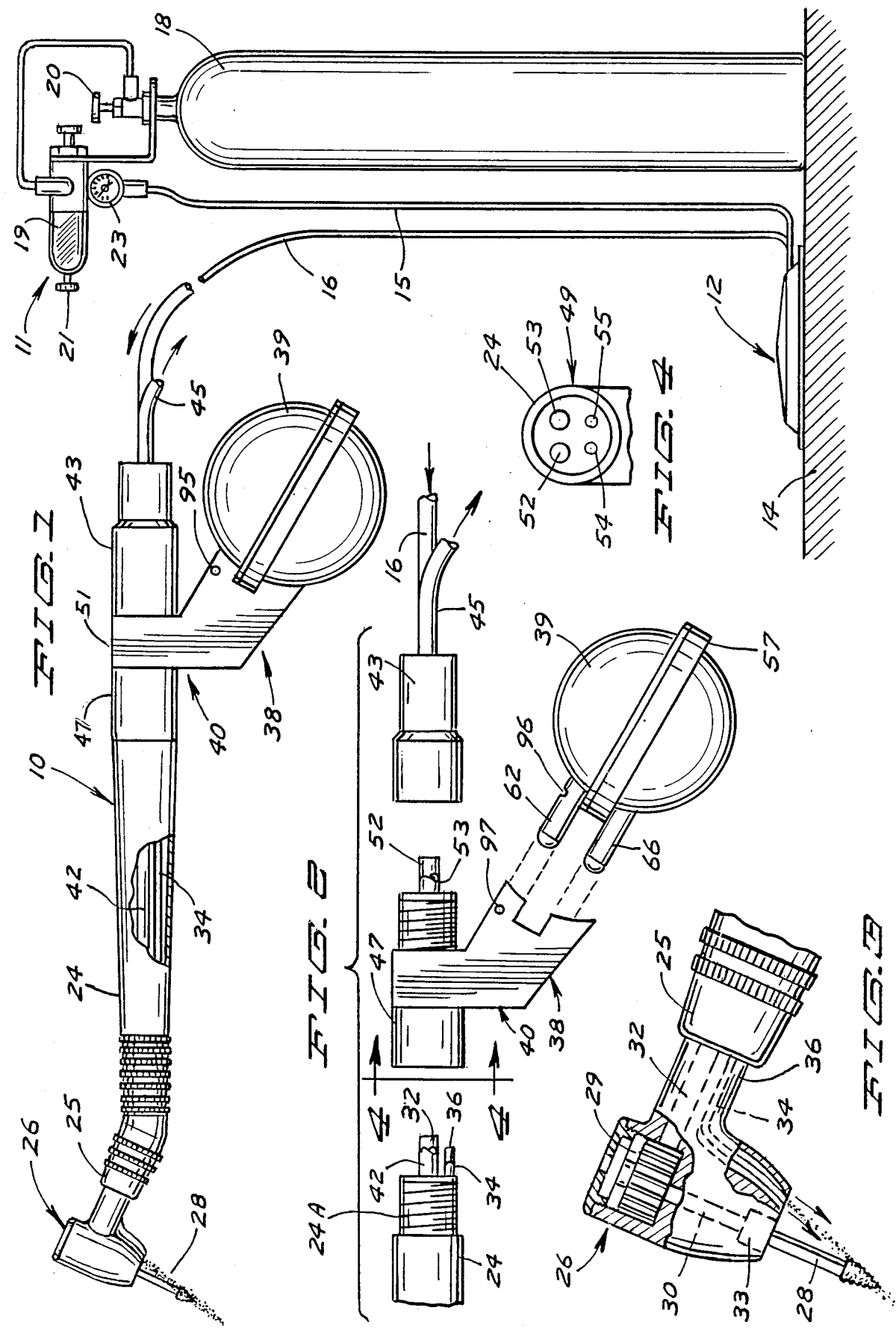

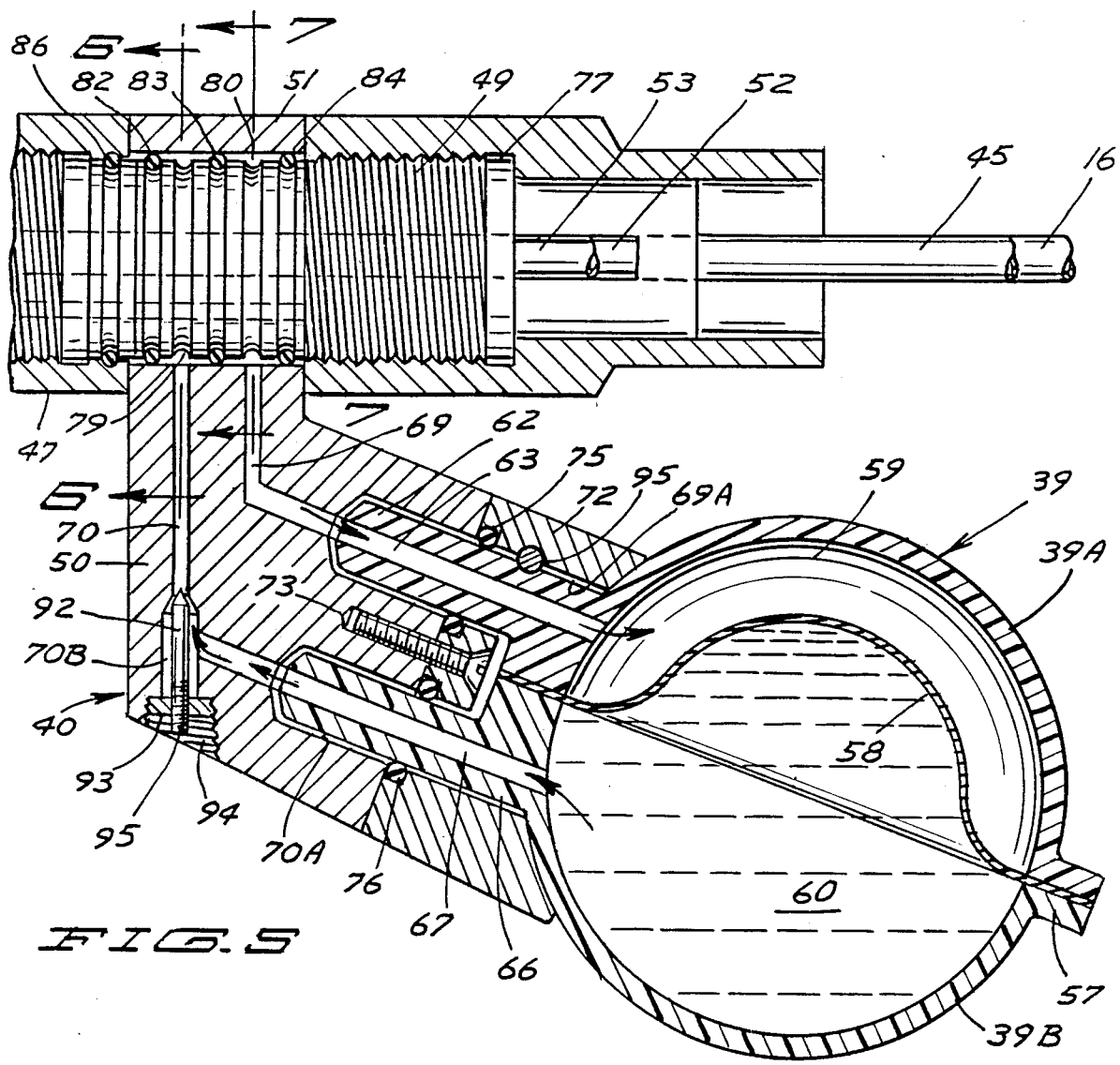
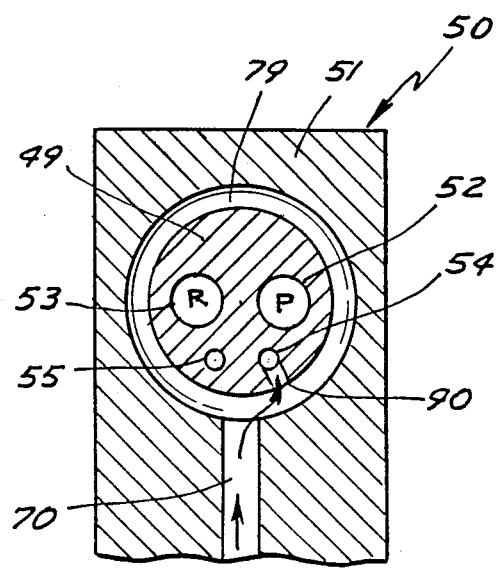
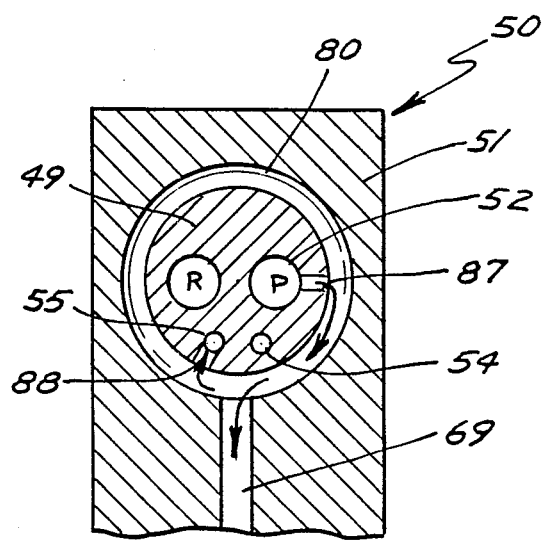

4,973,247

DENTAL HANDPIECE ASSEMBLY

BACKGROUND OF THE INVENTION

Maintaining a sterile medical environment is of utmost importance in the field of dentistry and oral surgery. This is to avoid not only the usual infection problem associated with an unsterile environment, but to avoid the potentially more serious problem of cross contamination from patient to patient. The appliance most intimate with the body and therefore the most apt to carry contamination to the patient is the dental handpiece and the working tool carried by it. Typical is the high speed rotary tool which is turbine driven and offers considerable time savings over the earlier types. This includes tools used in procedures such as drilling, cutting and cleaning. However, due to the frictional heat build-up and disintregation, a coolant or irrigant liquid is needed. Historically this is water provided by a building system. Water delivered to the tip of the appliance is not sterile. In addition, the tubing carrying the water cannot be sterilized. Upon turning the handpiece off, water can migrate back into the appliance and into the tubing. There it may harbor and nurture certain bacteria which will pass from one patient to the next.

This problem is addressed and virtually eliminated by the device shown and described in U.S. Pat. No. 4,470,812 issued Sept. 11, 1984 to Martens and Varnes. The device of that patent employs a cartridge carrying a sterile coolant. The cartridge has a flexible diaphram movable internally from one side to the other and dividing the cartridge into two chambers. Initially the chamber carrying the sterile coolant fills the cartridge. Water from the community water supply is introduced into the opposite chamber. As it is introduced into the one chamber, it forces the coolant out of the other through an outlet and through the dental handpiece to the oral cavity. A new cartridge is used for each patient. This results in only sterile coolant at proper temperature being introduced to the oral cavity for purposes of cooling the cutting handpiece and irrigating the surgical site, facilitating the removal of debris generated during the cutting procedure. The device of that patent is dependent upon the existence of a community water supply in order to provide water under pressure to displace the sterile solution in the cartridge for delivery to the oral cavity.

SUMMARY OF THE INVENTION

The invention pertains to a handpiece assembly including a compressed gas driven medical or dental tool of various types finding particular use in dental and surgical procedures. A disposable cartride is used to provide sterile liquid to the working site. High pressure gas or air normally flows through a drive air conduit to drive a turbine-type mechanism at the end of the handpiece, and then returns through a return air conduit for exhaust at an area remote from the handpiece. Part of the gas provided to drive the turbine is diverted into the propellant side of a cartridge having a flexible diaphram dividing it into a propellant chamber and a sterile coolant chamber. The air under pressure entering the propellant side of the cartridge displaces the diaphram to exert pressure upon the coolant which is then forced out of the cartridge outlet and into a coolant supply conduit of the handpiece. The need for the community water supply is eliminated. The unit can be operated using a community compressed air source, or a portable compressed gas source as provided in a pressurized tank. This later piece of equipment enables portability of a dental unit such that it can be self contained and independant of equipment provided at the working site.

IN THE DRAWINGS

FIG. 1 is a schematic view of a dental handpiece assembly that is self contained and includes a handpiece and a coolant apparatus according to the present invention;

FIG. 2 is an exploded assembly view of the coolant apparatus of the handpiece assembly of FIG. 1;

FIG. 3 is an enlarged view of the head of the dental handpiece of FIG. 1 with sections removed for purposes of illustration;

FIG. 4 is an end view of a portion of the coolant apparatus of FIG. 2 taken along the line 4—4 thereof.

FIG. 5 is an enlarged sectional view of the coolant apparatus of the handpiece assembly of FIG. 1;

FIG. 6 is a sectional view of a portion of the coolant apparatus of FIG. 5 taken along the line 6—6 thereof; and FIG. 7 is a sectional view of another portion of the coolant apparatus of FIG. 5 taken along the line 7—7 thereof.

DISCRIPTION OF A PREFERRED EMBODIMENT

Referring to the drawings, in FIG. 1 there is shown a stand alone dental assembly including a compressed gas driven dental or medical handpiece assembly 10 and a source or supply of compressed gas 11 with a remote control comprised as a foot control 12 supported on a floor 14 disposed between the gas supply 11 and the handpiece 10. A delivery hose 15 is connected between foot control 12 and the gas supply 11, and an inlet hose 16 is connected to the outlet of the foot control 12 and an inlet of the dental handpiece assembly 10. Gas supply 11 is shown as a portable stand alone unit, although a building source of compressed gas or air could be used as is commonly found in buildings equipped for dental or other medical procedures. The stand alone gas supply 11 imparts portability to the entire unit as for use in emergency situations. The gas supply can be a compressed inert gas such as nitrogen or, more typically, simply compressed air, and includes a pressure tank 18 having an attached pressure regulator 19. A tank valve 20 controls the flow of compressed gas to the regulator 19. Flow of gas through regulator 19 is controlled by regulator valve 21 and measured by pressure gauge 23. The foot control 12 typically provides for a variable control dependent upon foot pressure such that the pressure of the gas going through the inlet line 16 is adjusted as needed by the operator.

The dental drill assembly of FIG. 1 is independent of a community source of water as a coolant or propellant fluid. This eleminates the need for hook up to a community water supply and allows transport of the entire unit for performance of dental or medical procedures at locations previously inconvienent for use of the compressed gas driven handpiece.

The handpiece assembly 10 includes a handpiece comprised as an elongate tubular housing including a tubular handle portion 24 adapted to be gripped by the operator and a neck 25. Neck 25 is connected to a head assembly 26. The head assembly 26 carries a drill bit 28. As shown in FIG. 3, a high speed compressed gas driven turbine 29 is located in the head assembly 26. Turbine 29 is driven by compressed gas through a high pressure compressed gas conduit 32 in usual fashion. Other rotating or vibrating tools could be installed in head assembly 26.

The head 26, neck 25 and handle 24 can be of conventional dental construction whereby the sterile coolant apparatus of the invention as an adaptor is usable with most standard dental drill equipment. The high pressure turbine air drive conduit 32 and a return air conduit 42 extend the length of the hand piece, as do a chip air conduit 34 and a sterile coolant conduit 36 (FIG. 4). The various conduits extend outward of the downstream end of handle 24 and have outwardly extending tubular portions for connection to corresponding tubular receptacles of connector 40 of the coolant apparatus 38 of the invention. A hose coupler 43 connects to the upstream end of connector 40. Coupler 43 is attached to the high pressure air hose 16 for connection to the turbine air drive conduit 32, and to an exhaust air line 45 for exhaust of return air from the return air conduit 42.

The upstream end 24A of handle 24 is reduced in diameter and is exteriorly threaded. An interiorly threaded rotatable collar 47 secured to connector 40 connects to the end 24A of the handle 24.

Connector 40 includes a first fluid line or drive air line 52 for connecting the hose coupler to the turbine drive air conduit 32 of handle 24. A second fluid line or return air line 53 connects the return air conduit 42 to the exhaust air line 45 of the hose coupler 43. Connector 4 also has a chip air line 55 and a liquid line 54. A first connecting passage intersects the drive air line 52 and connects the fluid inlet or propellant side of the sterile coolant cartridge 39 to the compressible fluid or gas under pressure to provide a propellant force to the move the sterile fluid from the opposite side of the cartridge. A fluid port connects the drive air line 52 to the chip air conduit 34 of handle 24 whereby a portion of the pressurized gas is drawn off for a supply of gas to the chip air conduit. Connector 40 has a third fluid passage that connects the sterile fluid side of the coolant cartrige to the coolant delivery conduit of the handle 24.

As shown in FIGS. 2 and 4, the various fluid conduits extending from the downstream end of handle 24 are received in sockets or fluid line receptacles in the cylindrical body portion or insert member 49 of the connector 40. The first fluid line 52 has a receptacle for connection to the turbine drive air conduit 32. The second fluid line 53 has a receptacle for connection to the return air conduit 42. The third fluid line 54 is for connection to the sterile coolant cartridge, and the fourth fluid line 55 for connection to the chip air conduit. The various fluid conduits are connected in the respective receptacles when collar 47 is threaded to end portion 24A of the handle 24. The gas inlet and exhaust conduits 52 and 53 extend from the handle 24 through the connector 40 to the plug 43. Suitable receptacles are provided in the plug 43 for connection to the high pressure line 16 and exhaust line 45. Chip air conduit 55 and sterile coolant conduit 54 terminate in connector 40.

Insert member 49 of connector 40 contains various passages for connection to the propellant side 59 of the sterile coolant cartridge 39 and the sterile fluid side 60 of the cartridge as well as connection between the high pressure gas line and the chip air conduit.

Connector 40 includes an arm 50 connected to a tubular head 51 that rotatably encompasses the downstream end of insert member 49 which carries the various fluid flow passages. Sterile fluid cartridge 39 is formed as a relatively rigid sphere comprised of connected hemispheres 39A, 39B having flanged lips 57. The circumferences are joined at the flanges 57 by suitable means such as glue or ultrasonic welding. A flexible pressure communicating means or diaphram 58 extends through the interior of the cartridge 39 and is joined at its edges to the flanges 57, dividing the cartridge 39 into separate chambers 59, 60. The diaphram 58 is of sufficient size to extend between the opposite walls of the cartridge 39 thereby reducing the volume of either chamber to virtually zero while permitting the other to occupy virtually the entire volume of the cartridge 39. Diaphram 58 is of a flexible but relatively strong material such as a thin plastic. Diaphram 58 divides the cartridge 39 into a propellant chamber 59 and a sterile coolant chamber 60. In the initial condition of the cartridge 39 prepatory to use, sterile coolant chamber 60 is filled with sterile coolant fluid and fills the entire volume of the cartridge 39. Diaphram 58 is pressed against the interior wall of the hemisphere 39A which otherwise would partially define a volume of the propellant chamber 59.

An inlet means to the propellant chamber 59 of cartridge 39 is comprised as an elongate inlet prong 62 having an inlet passage 63. An outlet means from the sterile coolant chamber 60 of cartridge 39 is comprised of an elongate outlet prong 66 having a cartridge outlet passage 67.

The inlet and outlet prongs 62, 66 plug into end openings 69, 70 located at the end of the arm 50 (FIG. 5). The tip 72 of arm 50 has curved end portions for close accommodation of the circular elements of cartridge 39. Tip 72 is removable from the remainder of arm 50 by removal of screw 73 for the purpose of replacement of O-rings 75, 76 in the passages 69, 70 to maintain fluid type connection with the nozzles 62, 66.

The sleeve or head 51 of connector 50 is disposed in surrounding relationship to the forward or downstream portion of the insert 49. The rearward or upstream portion of insert 49 is exteriorly threaded for connection to plug 43 and carries an end gasket 77. Turbine drive air conduit 52 and return air conduit 52 extend the length of insert 49. The tubular extensions of conduits 52 and 53 plug into suitable recepticles provided in the plug 43 for connection to the turbine drive air supply lines 16 and the return air line 45.

The downstream or forward portion of insert 49 has two circumferential fluid passages, one for the sterile liquid and the other for compressed gas. Each passage is comprised as a circumferential groove formed superficially on body of the insert 49. The grooves are separated by O-rings located in suitable seats to prevent fluid leakage between passages. The O-rings also bear against the interior walls of the head 51 so that the connector 40 is rotatable with respect to the handle 24. This enables the operator to rotate the cartridge to the most convienent location while performing a dental procedure.

As shown in FIG. 5, there is a first fluid or sterile coolant passage 79 and a second fluid or compressed gas passage 80 located upstream of the fluid passage 79 and both comprised as circumferential grooves formed in the body of the insert member 49. First, second and third O-rings 82, 83, and 84 seated in circumferential seats formed in the barrel portion of insert member 49 isolate the fluid passages 79, 80.

A snap ring 86 is provided on the downstream end of insert member 49 at the juncture with collar 47. The O-rings 82-84 provide fluid seals and permit rotation of cartridge connector head 51 on the element 49. This permits positioning of the cartridge connector arm 50 in a position least obtrusive to the user of the dental handpiece.

As shown in FIG. 7, the circular fluid passage 80 is connected to the propellant fluid passage 69 which provides propellant or compressed gas to the propellant side 59 of the sterile fluid cartridge 39. The fluid passage 80 derives a supply of fluid or compressed gas from the turbine drive air conduit 52 of element 49. A first connecting passage or port 87 extends from the fluid passage 80 to intersect the drive air conduit 52. The port 87 is relatively small in comparison to the drive air conduit 52 such that only a small portion of the passing air is diverted from it. The air under pressure derived from the port 52 passes through the fluid passage 80 to the propellant air passage 69 to provide propellant to the propellant side 59 cartridge 39. A second connecting passage or port 88 is formed between the fluid passage 80 and the chip air conduit 55 of element 49. Chip air conduit 55 of insert 49 connects with the chip air conduit 53 of the handle 24. Air under pressure in the fluid passage 80 derived from the drive air conduit 52 passes through the second port 88 to provide chip air under pressure for that function.

FIG. 6 shows the downstream circular fluid passage 79 intersected by the coolant passage 70 of arm 50 leading from the coolant side of cartridge 39. A third fluid port 90 is formed between the downstream fluid passage 79 and the coolant conduit 54 of element 49. Liquid derived from the coolant side of cartridge 39, as indicated by the arrows in FIG. 6, travels through the fluid passage 70 of arm 50, into the circular fluid passage 79, through the third fluid port 90 and then to the liquid conduit 54 which communicates with the liquid conduit 32 of handpiece 24. The coolant will follow the same path independant of the rotational position of the arm 50 with respect to the insert element 49.

Means are provided to regulate the volumetric flow of coolant from the coolant cartridge. A slightly enlarged opening 70B is formed in the adaptor arm 50 in the passage 70 near a wall thereof. A valve stem 92 of a needle valve is located in the enlarged portion 70B in the neck thereof leading to the more restricted or normal size passage 70. One end of stem 92 has a pointed tip movable relatively into and out of blocking relationship to the passage 70 from the enlarged portion 70B. The other end of stem 92 is fixed to an threaded head 93 which is threadably engaged in an internaly threaded opening 94 accessible from outside of the arm 50 with a screw driver or like tool. The outer end of the stem 92 can have a slot 95 for rotation with a typical screw driver. Rotation of the stem 92 moves the tip of the valve stem 92 more or less into and out of blocking engagement with the passage 70 to control the volumetric flow of fluid.

The needle valve 92 can be adjusted in accordance with the foot control 12 to provide a proper amount of coolant flow. The operator engages the foot control 12 to a maximum pressure as is determined by the valve 21 on tank 18. The operator then adjusts the needle valve 92 to deliver the maximum desired amount of flow of coolant. Following this calibration, any lesser amount of pressure as regulated by the foot control 12 will result in a proportionate lesser amount of flow of coolant from the cartridge 39.

Means are provided for releasabily securing the capsule 39 with respect to the capsule connector arm 50. A slidable locking pin 95 engages in an opening 97 in arm 50 and a groove 96 in one of the prongs 92 of capsule 39 (see FIGS. 1 and 2). When the prongs of the capsule 39 are inserted in the legs of connector arm 50, the groove 96 is lined with the opening 97 in the adaptor arm 50. The pin 95 is inserted through both, having a diametric portion sufficient to fill the groove 96 and opening 97 and hold the capsule 39 with respect to the cartridge connector 50. Lateral movement of the pin 95 out of engagement with groove 96 permits removal or insertion of a cartridge 39.

The handpiece assembly is usable to dispense any potential coolant, irrigation and lavage type solutions in addition to sterile water and saline solutions. The cartridge could be filled with a high level disinfectant solution to disinfect the coolant channel of the handpiece where sterilization is otherwise unavailable.

In the use of the invention, there is provided a source of compressible fluid, such as an inlet gas as nitrogen under pressure, or compressed air. The supply can be from a portable gas tank, a bank of interconnected tanks, a building or community supply of compressed gas of the like, capable of providing a continuous supply of compressed gas at approximately thirty psi or other suitable pressure to operate the dental equipment. The gas supply is connected to the turbine air conduit 32 of handpiece assembly 10 through the cartridge connector 50. A full cartridge 39 is installed on the cartridge connector 50, a new cartridge being used for each patient. The coolant chamber 60 of the cartridge is full, occupying virtually the entire volume of the cartridge. The coolant can be sterile water or a medicated or anticeptic solution. Acutation of gas supply through control 12 provides gas under pressure to operate tubine 29 for the purpose of driving a high speed cutting or drilling tool. Simultaneously a part of the turbine drive gas is diverted to the propellant chamber 59 of cartridge 39, imposing a pressure upon diaphram 58 and moving it whereby coolant liquid under pressure is moved through the various fluid passages to the fluid conduit 36 of handpiece 23 and then out of the head 26 of the dental tool. The amount of coolant liquid delivered according to the gas pressure is calibrated by needle valve 92. Simultaneously also, chip air under pressure is provided as a result of a further diversion of gas from the turbine drive air conduit. The cartridge connector 50 is rotated relative to the handpiece 24 to a position most convienient for the operator. A dental drilling tool has been illustrated. Other tools such as an ultrasonic scaler.

While there has been shown and described a preferred embodiment according to the invention, it will be apparent that certain deviations could be had from the embodiment shown without departing from the scope of the invention.

The embodiments of the invention in which an exclusive property or privilege is claimed are defined as follows:

1. A medical gas powered handpiece assembly releasably connectable to a supply of gas under pressure, comprising:

an elongate tubular handpiece having a downstream discharge end carrying a rotatable working tool and a pressurized gas drive means for rotation of the working tool, and an upstream inlet end;

a drive air conduit extending from the upstream end of the handpiece to the downstream discharge end for carrying pressurized gas to the drive means, and means on the upstream end of the drive air conduit releasably connectable to said supply of gas under pressure;

a discharge drive air conduit extending from the downstream end of the handpiece to a remote location for discharge of gas under pressure from the drive means;

a fluid delivery conduit in the handpiece having an outlet end at the discharge end of the handpiece positioned for discharge of liquid under pressure proximate an intended working site of the working tool, and an inlet terminal on the handpiece;

a disposable fluid cartridge comprised as a housing having an inlet chamber and an outlet chamber and including movable pressure communicating means separating the inlet chamber and the outlet chamber in fluid tight relationship and movable with respect to the housing to vary the volumes of the chambers in reciprocal fashion;

inlet means to the inlet chamber of the cartridge;

outlet means to the outlet chamber of the cartridge;

a first port intersecting the drive air conduit;

a first fluid passage means connected to the first port and to the inlet means of the cartridge to supply gas under pressure diverted from the drive air conduit to the inlet chamber of the cartridge for purposes of displacing the movable pressure communicating means;

a second fluid passage means connecting the inlet means of the fluid delivery conduit and releasably connecting the outlet means of the cartridge;

said outlet chamber of the cartridge carrying an initial supply of liquid intended to be displaced and discharged through the second fluid passage and the fluid delivery conduit upon introduction of gas under pressure in the inlet chamber of the cartridge, and means to control supply of compressed gas through the drive air conduit.

2. The handpiece assembly of claim 1 including: a chip air conduit having an outlet end at the discharge end of the handpiece positioned for discharge of gas under pressure proximate the intended working site of the working tool, and an inlet terminal in the handpiece, and a second port connecting the inlet terminal of the chip air conduit and the first passage way whereby a portion of the pressurized gas is diverted from the drive air conduit to the chip air conduit through the first fluid passageway.

3. The handpiece assembly of claim 2 wherein: said handpiece includes a tubular barrel portion, said first fluid passage means including a first circumferential groove formed on the tubular barrel portion, said first and second ports formed in the first circumferential groove; said second fluid passage means including a second circumferential groove formed in the barrel portion and having an opening to the fluid delivery conduit.

4. The handpiece assembly of claim 3 including: a connector releasably connecting the fluid cartridge to the handpiece, said connector including a sleeve in surrounding relationship to the tubular barrel portion of the handpiece and rotatable with respect to the handpiece, sealing means between the sleeve and the barrel portion of the handpiece positioned for fluid isolation of the first and second circumferential grooves, arm means connected at one end to the sleeve and releasably connectable at the other end to the fluid cartridge, said arm means having a first fluid passage connecting the first circumferential groove and the inlet means to the inlet chamber of the cartridge for delivery of gas under pressure to the inlet side of the cartridge, and a second fluid passage connecting the second circumferential groove to the outlet means of the cartridge for delivery of fluid from the outlet chamber of the cartridge to the fluid conduit of the handpiece.

5. The handpiece assembly of claim 4 wherein: said drive means includes a compressed gas driven turbine.

6. The handpiece assembly of claim 5 wherein: said movable pressure communicating means of the fluid cartridge is comprised as a flexible diaphram extended across the interior of the housing and of sufficient dimension to move within the housing to reduce the volume of either chamber to virtually zero.

7. The handpiece assembly of claim 6 wherein: said cartridge is comprised of two hemispheres circumferentially joined, said diaphram being connected at the juncture of the hemishperes.

8. The handpiece assembly of claim 7 wherein: said hemispheres are formed of a relatively rigid material.

9. The handpiece assembly of claim 8 wherein: said inlet means to the inlet chamber is comprised as a first prong having a inlet passage, said outlet means from the outlet chamber comprised as a second prong with an outlet passage, said connector arm means comprised as an arm having said first and second fluid passages and receptacle openings for releasably connecting the inlet and outlet prongs of the cartridge to the first and second passages.

10. The handpiece assembly of claim 9 including: a needle valve connected in the outlet passage for control of the volumetric flow of fluid from the outlet chamber of the cartridge.

11. The handpiece assembly of claim 10 including: a compressed gas tank for containment of a supply of compressed gas under pressure;

regulator means connected to the compressed gas tank;

a gas delivery line connected at one end to the regulator means and at the opposite end to the means on the upstream end of the drive air conduit.

12. An adaptor for connecting to a dental handpiece to provide sterile fluid solution to the handpiece discharge under pressure from a propellant gas, said dental handpiece of the type having a tubular body, a neck connected to the downstream end of the body, and a head connected to the neck, means in the head for connection of a rotary working tool, a drive air conduit, a return air conduit, a chip air conduit and a liquid conduit all extending from the upstream inlet end of the body to the downstream discharge end, said adaptor comprising:

a tubular insert member having an upstream end and a downstream end, a drive air line extended the length of the tubular insert member adapted for connection to a compressed gas supply at the upstream end thereof, a return air line extending the length of the tubular insert member, a chip air line open at the downstream end of the tubular member and terminating at an interior location therein, and a liquid line open at the downstream end of the insert member and terminating at an interior location thereon;

said drive air line, return air line, chip air line and liquid line having receptacles at the downstream end of the insert member for receipt of the drive air conduit, return air conduit, chip air conduit and liquid conduit of the dental handpiece in plug type relationship;

a connector for connection to the tubular insert member of a disposable fluid cartridge of the type comprised as a housing having an inlet chamber and an outlet chamber and including movable pressure communicating means separating the inlet chamber and the outlet chamber in fluid type relationship and movable with respect to the housing to vary the volumes of the chambers in reciprocal fashion, inlet means to the inlet chamber of the cartridge, outlet means to the outlet chamber of the cartridge, said outlet chamber being initially filled with a sterile liquid and occupying virtually the entire volume of the cartridge with said inlet chamber volume reduced to virtually zero;

said insert member having a first port intersecting the drive air conduit, a first fluid passage connecting to the first port;

a second fluid passage connected to the liquid delivery line;

arm means having an inlet channel connected to the first fluid passage and connectable to the inlet means of the fluid cartridge so that some compressed gas from the drive air line is diverted to the inlet chamber of the cartridge to function as a propellant to move the liquid out of the outlet chamber;

said arm means having an outlet channel connected to the second fluid passage of the insert member and connectable to the outlet means of the fluid cartridge to allow liquid to flow from the outlet side of the cartridge to the fluid line of the insert member upon introduction of gas under pressure to the inlet side of the cartridge; and means for removable connection of the fluid cartridge to the arm means.

13. The adaptor of claim 12 wherein: said insert member has a tubular portion with a first circumferential groove comprising said first fluid passage and a second circumferential groove comprising said second fluid passage, said arm means including a sleeve in surrounding fluid tight relatonship to the first and second circumferential grooves, said inlet and outlet channels of the arm means communicating with the first and second circumferential grooves.

14. The adaptor of claim 13 wherein: said first port is located in the first circumferential groove and including a second port located in the first circumferential groove and communicating with the chip air conduit for diverting a portion of the gas passing through the drive air conduit to the chip air line and to the chip air conduit to provide gas under pressure to the discharge end of the chip air conduit.

15. The adaptor of claim 14 wherein: said second circumferential groove has a port open to the end of the fluid line.

16. The adaptor of claim 14 wherein: said disposable fluid cartridge is the type having a first prong associated with the inlet means and a second prong associated with the outlet means, and wherein: said arm means includes an enlarged receptical portion as part of the inlet channel and an enlarged receptical portion as part of the outlet channel for the receipt of the first and second prongs of the fluid cartridge.

17. The adaptor of claim 15 including: valve means associated with the outlet channel of the arm means in order to regulate the volumetric flow of fluid from the outlet chamber of the disposable fluid cartridge.

18. The adaptor of claim 17 wherein said valve means is comprised as a needle valve.

19. The adaptor of claim 18 including: a plurality of O-rings surrounding the barrel portion of the insert member and positioned to isolate the first and second fluid passages and permit rotation of the arm with respect to the insert member.

20. A dental handpiece assembly comprising:
a tubular housing having a downstream end and an upstream end;
a head assembly at the downstream end, having a reciprocating compressed gas driven motor for connection to a working tool to perform a dental procedure upon a patient;
said tubular housing carrying a drive air conduit, return air conduit, and a liquid conduit;
said drive air conduit extending from the downstream end of the housing to the head assembly to provide pressurized gas to drive the rotary motor in the head assembly, the end of the drive air conduit at the upstream end of the housing having means for connection to a supply of gas under pressure;
said liquid conduit having a downstream discharge end at said head assembly, and an upstream terminal end;
a disposable liquid cartridge comprised as a second housing having a movable flexible diaphram dividing the interior of the housing into an inlet chamber and an outlet chamber and movable with respect to the housing interior to vary the volumes of the chambers in reciprocal fashion, and inlet means to the inlet chamber, and an outlet means to the outlet chamber;
first fluid passage means intersecting the drive air conduit of the tubular housing to divert a portion of compressed gas from it, and means for releasable connection of the first fluid passage means to the inlet means of the inlet chamber of the liquid cartridge;
second fluid passage means connected at the terminal upstream end of the fluid line and releasably connectable to the outlet means of the liquid cartridge to provide passage of liquid from the outlet chamber of a liquid cartridge of the fluid line upon introduction of compressed gas to the inlet chamber of the cartridge.

21. The dental handpiece of claim 20 including; a chip air conduit in the tubular housing having a downstream end terminating in said head assembly and an upstream terminal end in the tubular housing, said first fluid passage having a fluid connection to the upstream terminal end of the chip air conduit to provide gas under pressure to the chip air conduit.

* * * * *

UNITED STATES PATENT AND TRADEMARK OFFICE
CERTIFICATE OF CORRECTION

PATENT NO. : 4,973,247

DATED : November 27, 1990

INVENTOR(S) : DeWayne L. Varnes and Leslie V. Martens

It is certified that error appears in the above-identified patent and that said Letters Patent is hereby corrected as shown below:

Title Page:
Abstract, line 4, "irriagate" should be --- irrigate ---.

Col. 1, line 53, "cartride" should be --- cartridge ---.

Col. 2, line 2, "later" should be --- latter ---.

Col. 2, line 27, "Discription" should be --- Description ---.

Col. 2, line 58, "eleminates" should be --- eliminates ---.

Col. 2, line 61, "inconvienent" should be --- inconvenient ---.

Col. 3, lines 31 and 32, "Connector 4" should be ---Connector 40---.

Col. 3, lines 35 and 36, "force to the move' should be ---force to move---.

Col. 3, line 42, "cartrige" should be --- cartridge ---.

Col. 4, line 18, "prepatory" should be --- preparatory ---.

Col. 4, line 44, "Turbine drive air conduit 52" should be
--- Turbine drive air conduit 32 ---.
"return air conduit 52" should be --- return air conduit 42 ---.

Col. 4, line 59, "convienent" should be --- convenient ---.

Col. 5, line 41, "independant" should be --- independent ---.

Col. 5, line 52, "an threaded" should be --- a threaded ---.

Col. 5, line 53, "internaly" should be --- internally ---.

Col. 6, line 3, "releasabily" should be --- releasably ---.

Col. 6, line 5, "slidable" should be --- slideable ---.

Col. 6, line 39, "tubine 29" should be --- turbine 29 ---.

UNITED STATES PATENT AND TRADEMARK OFFICE
CERTIFICATE OF CORRECTION

PATENT NO. : 4,973,247

DATED : November 27, 1990

INVENTOR(S) : DeWayne L. Varnes and Leslie V. Martens

It is certified that error appears in the above-identified patent and that said Letters Patent is hereby corrected as shown below:

Col. 6, line 53, "convienient" should be --- convenient ---.

Col. 8, line 24, "hemishperes" should be --- hemispheres ---.

Col. 8, line 30, "a inlet passage" should be --- an inlet passage ---.

Col. 9, line 49, "relatonship" should be --- relationship ---.

Col. 10, line 16, insert "means" after --- arm ---.

Col. 10, line 55, "of" (second occurrence) should be --- to ---.

Col. 10, line 58, "including;" should be --- including:---.

Signed and Sealed this

Eleventh Day of August, 1992

*Attest:*

DOUGLAS B. COMER

*Attesting Officer*     *Acting Commissioner of Patents and Trademarks*